United States Patent
Oyama et al.

(10) Patent No.: US 7,670,205 B2
(45) Date of Patent: Mar. 2, 2010

(54) CROTCH-POSSESSING CORRECTIVE GARMENT

(75) Inventors: Makoto Oyama, Kyoto (JP); Atsuko Kawamura, Kyoto (JP); Yoshiaki Nakagawa, Kyoto (JP)

(73) Assignee: Wacoal, Corp., Kyoto (JP)

( * ) Notice: Subject to any disclaimer, the term of this patent is extended or adjusted under 35 U.S.C. 154(b) by 483 days.

(21) Appl. No.: 10/596,040

(22) PCT Filed: Nov. 28, 2003

(86) PCT No.: PCT/JP03/15284

§ 371 (c)(1),
(2), (4) Date: May 25, 2006

(87) PCT Pub. No.: WO2005/051110

PCT Pub. Date: Jun. 9, 2005

(65) Prior Publication Data

US 2008/0268749 A1    Oct. 30, 2008

(51) Int. Cl.
*A41C 1/04* (2006.01)
*A41D 1/06* (2006.01)
(52) U.S. Cl. .................. 450/97; 2/69; 272/119
(58) Field of Classification Search .......... 2/227, 2/228, 238, 69; 450/97, 98, 100, 101, 106, 450/107, 112, 122–124, 130–131, 151; 272/119
See application file for complete search history.

(56) References Cited

U.S. PATENT DOCUMENTS

| | | | | |
|---|---|---|---|---|
| 3,894,542 A | * | 7/1975 | Sacristan | 450/123 |
| 5,109,546 A | * | 5/1992 | Dicker | 2/70 |
| 5,960,474 A | * | 10/1999 | Dicker et al. | 2/69 |

FOREIGN PATENT DOCUMENTS

| | | |
|---|---|---|
| JP | 61-124611 A | 6/1986 |
| JP | 2182903 | 7/1990 |
| JP | 6007394 | 1/1994 |
| JP | 06-173101 A | 6/1994 |
| JP | 10-008303 A | 1/1998 |
| JP | 11-061516 A | 3/1999 |
| JP | 2000-135233 | 5/2000 |
| JP | 2001-104369 A | 4/2001 |
| JP | 2001-192903 A | 7/2001 |
| JP | 2002-235207 A | 8/2002 |
| WO | WO-99/58007 A1 | 11/1999 |

\* cited by examiner

*Primary Examiner*—Gloria Hale
(74) *Attorney, Agent, or Firm*—Darby & Darby

(57) ABSTRACT

An object of the present invention is to provide a girdle which can improve posture by acting on the muscles around the pelvis, is easy to handle and can be worn with no uncomfortable feeling. An example of the present invention is a girdle (short girdle and long girdle) containing, in an area fitting over a wearer's body, a tightening portion for which the magnitude of a tightening force varies with areas. When the garment is being worn, the tightening fabric portion extends from the vicinity of an upper part of the buttocks cleft, passing the vicinities of upper parts of the right and left buttocks, to the vicinities of the right and left greater trochanters, and the tightening fabric portion may be made of material having a tightening force. Moreover, a body front tightening fabric portion is provided at the front of the garment.

20 Claims, 20 Drawing Sheets

PIRIFORM MUSCLE

EXTERNAL OBLIQUE MUSCLE

US 7,670,205 B2

CROTCH-POSSESSING CORRECTIVE GARMENT

CROSS REFERENCE TO PRIOR RELATED APPLICATION

This application is a U.S. national phase application under 35 U.S.C. §371 of International Patent Application No. PCT/JP2003/015284, filed Nov. 28, 2003, which is incorporated by reference herein. The International Application was published in Japanese on Jun. 9, 2005 as International Publication No. WO 2005/051110 A1 under PCT Article 21(2).

TECHNICAL FIELD

The present invention relates to a crotch-possessing corrective garment such as a girdle for posture correction.

BACKGROUND ART

As a crotch-possessing corrective garment for posture correction, for example, there is known the girdle described in Japanese Patent Application Laid-Open No. 2001-192903. There, a belt-shaped strong tightening portion which generates a strong tightening force is provided from the sacrum along the direction of muscle fibers of the gluteus maximus, which functions to weaken forward curvature of the lumbar flexure for the main purpose of stabilizing the hip joint. Further, as the girdle used for the purpose of treating lumbago, straightening the spine and the like, there are known the girdles disclosed in, for example, Japanese Patent Application Laid-Open No. H6-173101, Japanese Patent Application Laid-Open No. H10-8303, Japanese Patent Application Laid-Open No. 2001-104369, and Japanese Patent Application Laid-Open No. 2001-192903.

The girdle disclosed in Japanese Patent Application Laid-Open No. H6-173101 is attached with belt-shaped pelvis-correcting pieces for tightening the lumbar region in a horizontal direction, and Japanese Patent Application Laid-Open No. H10-8303 discloses a girdle having belt-shaped fixings attached thereto. Furthermore, Japanese Patent Application Laid-Open No. 2001-104369 discloses a girdle in which bands made of a stretchable material are wound around the lumbar region. Specifically, it discloses a girdle for treating lumbago, which has right and left bands that intersect with each other at the back of a wearer's body from the right thigh portion to a left lumbar region and from the left thigh portion to a right lumbar region, wherein the entire pelvis is wrapped by the stretchable bands.

However, in the conventional girdles, the effect of posture correction is small and handling is difficult. For example, regarding the girdles disclosed in Japanese Patent Application Laid-Open No. H6-173101 and Japanese Patent Application Laid-Open No. H10-8303, belt-shaped correcting pieces or fixings which are separate from the main body of the garment (or have one end thereof sewn onto the main body) are used, and thus handling is difficult. In the girdle disclosed in Japanese Patent Application Laid-Open No. 2001-104369 as well, stretchable bands which are separate from the main body of the garment are used; thus there is uncomfortable feeling when wearing the garment and handling is not easy. Furthermore, the main objective of these girdles is to treat lumbago, but the effect of improving postural balance is low.

As described above, most of the conventional posture-correction-type garments are mainly stoop-correcting garments for the upper half of the body and lumbago-preventing garments for the lower half of the body, but there have been no attempts to improve the posture of the whole body by acting around the pelvis.

An object of the present invention is to provide a crotch-possessing corrective garment which can improve posture by acting on the pelvis with the same force as the force of muscles around the pelvis, and furthermore is easy to handle and can be worn with no uncomfortable feeling.

DISCLOSURE OF THE INVENTION

According to the research of the present inventors, there are many people having poor posture balance due to the pelvis being tilted forward. Therefore, with people having various problems with their postural balance as monitors, taping was performed along the muscles around the pelvis (the piriform muscles, iliopsoas muscles, sacrospinalis muscles, external oblique muscles, and the like), and changes in posture and the subjective feeling (feeling when worn) were examined.

As a result, it was ascertained that for people whose pelvis tends to be tilted forward in particular, provision of a support on the piriform muscle leads to a large posture correction effect, and when it is used in combination with a support on the external oblique muscle, better effects can be expected. On the other hand, no significant posture correction effects were observed for the sacrospinalis muscles.

Of the muscles around the pelvis, the positions of the piriform muscles and the external oblique muscles are as shown by the hatching in FIG. 1A and FIG. 1B. As shown in FIG. 1A in which the pelvis is viewed from the rear, the piriform muscle is a muscle positioned on a hip joint and is for rotating the hip joint outwardly. As shown in FIG. 1B in which the body is viewed from the front, the external oblique muscle is positioned across a broad area from the lumbar region over the abdomen and up to the chest.

Furthermore, the positions of the greater trochanters, the ilia, and the sacrum are as illustrated in FIG. 2A through FIG. 2D. FIG. 2A shows the skeleton for the case of viewing the body from the front, FIG. 2B shows the external form of the body in this case, FIG. 2C shows the skeleton for the case of viewing the body from the rear, and FIG. 2D shows the external form of the body in this case. As shown in FIG. 2A and FIG. 2B, the ilium is positioned on the outside at the top of the pelvis, and the greater trochanter is positioned at the top of a femur as shown in FIG. 2C and FIG. 2D. Further, as shown by the hatching in FIG. 2C and FIG. 2D, the sacrum is positioned at the bottom of the lumbar flexure in the center of the pelvis.

A crotch-possessing corrective garment according to the present invention contains: a tightening portion in an area which fits over a wearer's body, the tightening portion extending, when the garment is being worn, from the vicinity of an upper part of the buttocks cleft, passing the vicinities of upper parts of the right and left buttocks, to the vicinities of the right and left greater trochanters; and a body front tightening portion made of material having a tightening force and extending, when the garment is being worn, from above the crotch at the front center toward above the right and left of the crotch.

Further, the crotch-possessing corrective garment according to the present invention may contain: in an area fitting over a wearer's body, a tightening portion for which the magnitude of a tightening force varies with areas, the tightening portion extending, when the garment is being worn, from the vicinity of an upper part of the buttocks cleft, passing the vicinities of upper parts of the right and left buttocks, to the vicinities of the right and left greater trochanters; and a body front tightening portion made of material having a tightening force and extending, when the garment is being worn, from above the crotch at the front center toward above the right and left of the crotch.

According to the present invention, the tightening portion which applies a tightening force to the wearer's body is provided in an area fitting over the wearer's body so as to form a constituent of the garment itself; thus handling is easy and the feeling when worn is not impaired. Moreover, when the garment is worn, the tightening portion, which extends from the vicinity of an upper part of the buttocks cleft, passing the vicinities of upper parts of the right and left buttocks, to the vicinities of the right and left greater trochanters, functions so as to support the piriform muscles in a longitudinal direction and push a somewhat lower part of the sacrum from the rear. Specifically, a strong tightening force acts in an area which extends from the vicinity of an upper part of the buttocks cleft, passing the vicinities of upper parts of the right and left buttocks, to the vicinities of the right and left greater trochanters; thus a force acts on the buttocks and the tension in the flank portions is reduced. Therefore, there is an action similar to allowing the buttocks to strain the muscles thereof to close the anus. Further, since the tightening portion further has a body front tightening portion which extends from above the crotch at the front center toward above the right and left of the crotch, there is an action on the external oblique muscles as well, whereby posture can be further improved. Specifically, a force in a downward direction which is generated in the vicinity of the upper part of the buttocks cleft and a force in an upward direction generated in the body front tightening portion generate a rotating force which acts to lift the pelvis that is tilted forward. To this end, as to power difference between the crotch area and a waist area at a body front portion, it is preferable for the tightening force to become strong gradually toward the waist portion as this will increase the upward force.

Here, regarding the tightening force in the vicinities of the greater trochanters, first the tightening force is applied to the greater trochanters, whereby a force directed from the flanks (outside) to the inside is generated. Accordingly, the position of the pelvis is fixed to the right position. In other words, the tightening force at the greater trochanters has a function of stabilizing the pelvis at a fixed position. Moreover, if the tightening force is generated on the greater trochanters, the pelvis is fixed to the right position as just described, and hence "the force pushing the pelvis" in the tightening portion which is convex upwardly toward the vicinity of the upper part of the buttocks cleft acts effectively, with the right position of the pelvis as the supporting point. In this manner, since the pelvis is fixed to the right position, the pelvis can rotate smoothly.

The crotch-possessing corrective garment according to the present invention may contain: in areas fitting over a wearer's body, a pair of right and left tightening portions for which the magnitude of a tightening force varies with areas, each of the tightening portions extending, when the garment is being worn, from the vicinity of the right or left greater trochanter to the vicinity of an upper part of the right or left buttocks such as to extend toward the vicinity of an upper part of the buttocks cleft; and a body front tightening portion made of material having a tightening force and extending, when the garment is being worn, from above the crotch at the front center toward above the right and left of the crotch.

According to the present invention, the pair of right and left tightening portions which apply a tightening force to the wearer's body are provided in right and left areas fitting over the wearer's body so as to form a constituent of the garment itself; thus handling of the garment is easy and the feeling when worn is not impaired. Moreover, when the garment is worn, each of the pair of right and left tightening portions, which extends from the vicinity of an upper part of the buttocks cleft, passing the vicinities of upper parts of the right and left buttocks, to the vicinities of the right and left greater trochanters, functions so as to support the piriform muscles and push a somewhat lower part of the sacrum from the rear. Specifically, a strong tightening force acts in an area which extends from the vicinity of an upper part of the buttocks cleft, passing the vicinities of upper parts of the right and left buttocks, to the vicinities of the right and left greater trochanters; thus a force acts on the buttocks and the tension in the flank portions is reduced. Therefore, there is an action similar to allowing the buttocks to strain the muscles thereof to close the anus. Further, since the tightening portion further has a body front tightening portion which extends from above the crotch at the front center toward above the right and left of the crotch, there is an action on the external oblique muscles as well, whereby posture can be further improved. Specifically, a force in a downward direction which is generated in the vicinity of the upper part of the buttocks cleft and a force in an upward direction generated in the body front tightening portion generate a rotating force which acts to lift the forward-tilted pelvis. To this end, as to power difference between the crotch area and a waist area at a body front portion, it is preferable for the tightening force to become strong gradually toward the waist portion as this will increase the upward force.

In the crotch-possessing corrective garment according to the present invention, the tightening portion, which extends, when the garment is being worn, from the vicinity of the upper part of the buttocks cleft, passing the vicinities of the upper parts of the right and left buttocks, to the vicinities of the right and left greater trochanters, is preferably configured such that the tightening force is strongest in the vicinity of the upper part of the buttocks cleft. Accordingly, the strong tightening force acts in the vicinity of the upper part of the buttocks cleft, and at the same time acts in a direction passing the vicinities of the upper parts of the right and left buttocks and extending toward the vicinities of the right and left greater trochanters; thus there is an action on the piriform muscles to further improve the posture.

In the crotch-possessing corrective garment according to the present invention, the tightening portion, which extends, when the garment is being worn, from the vicinity of the upper part of the buttocks cleft, passing the vicinities of the upper parts of the right and left buttocks, to the vicinities of the right and left greater trochanters, is preferably configured such that the tightening force is strongest in the vicinity of the upper part of the buttocks cleft and gradually weakens in a direction passing the vicinities of the upper parts of the right and left buttocks and extending toward the vicinities of the right and left greater trochanters. Accordingly, the strong tightening force acts in the vicinity of the upper part of the buttocks cleft, and at the same time acts in the direction passing the vicinities of the upper parts of the right and left buttocks and extending toward the vicinities of the right and left greater trochanters; thus there is an action on the piriform muscles to further improve the posture.

The crotch-possessing corrective garment according to the present invention may further have thigh portions which fit over the wearer's thighs, wherein the tightening portion further extends from the vicinities of the greater trochanters along the outer borders of the thigh portions, and moreover the tightening portion further reaches the ankles. Accordingly, there are actions on the muscles of the greater trochanters and around the pelvis, and the function of improving the posture of the whole body is increased.

In the crotch-possessing corrective garment according to the present invention, the tightening portion preferably has a shape which is curved upward in the vicinity of the upper parts of the buttocks when the garment is being worn. Accordingly, the feeling when worn can be further improved.

In the crotch-possessing corrective garment according to the present invention, when the garment is being worn, the tightening portion preferably has an upper side tightening portion positioned on an upper side, and a lower side tightening portion which is positioned on a lower side and has a strong tightening force. Accordingly, the upper side and lower side tightening portions collaborate with each other to act suitably on the piriform muscles, and the function of improving the posture of the wearer whose posture is tilted forward can be further increased.

In the crotch-possessing corrective garment according to the present invention, the tightening portion preferably forms a belt shape, and is formed through power change in a single piece of knitted fabric. Furthermore, the crotch-possessing corrective garment according to the present invention is, for example, any one of a girdle, spats, a bathing suit, tights, a pantyhose, sports tights, a leotard, a body suit, men's pants, or the like.

BEST MODES FOR CARRYING OUT THE INVENTION

Figure 1A:
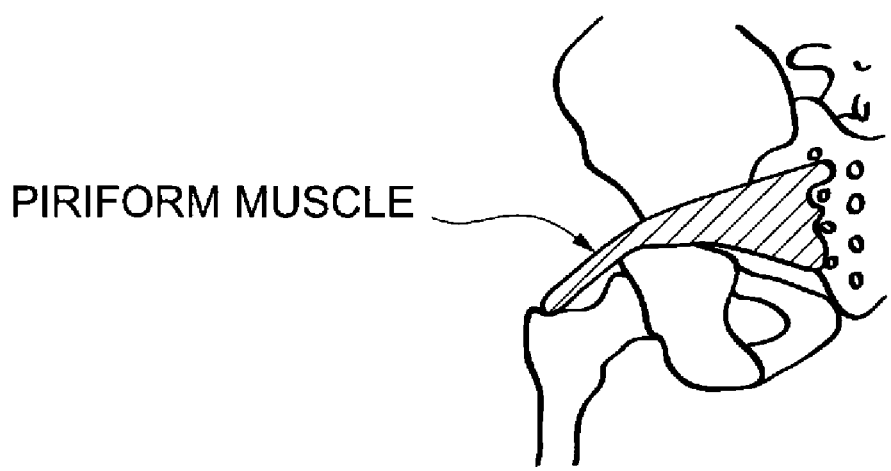
FIG. 1A is a figure for explaining the position of the piriform muscle of a body.
Figure 1B:
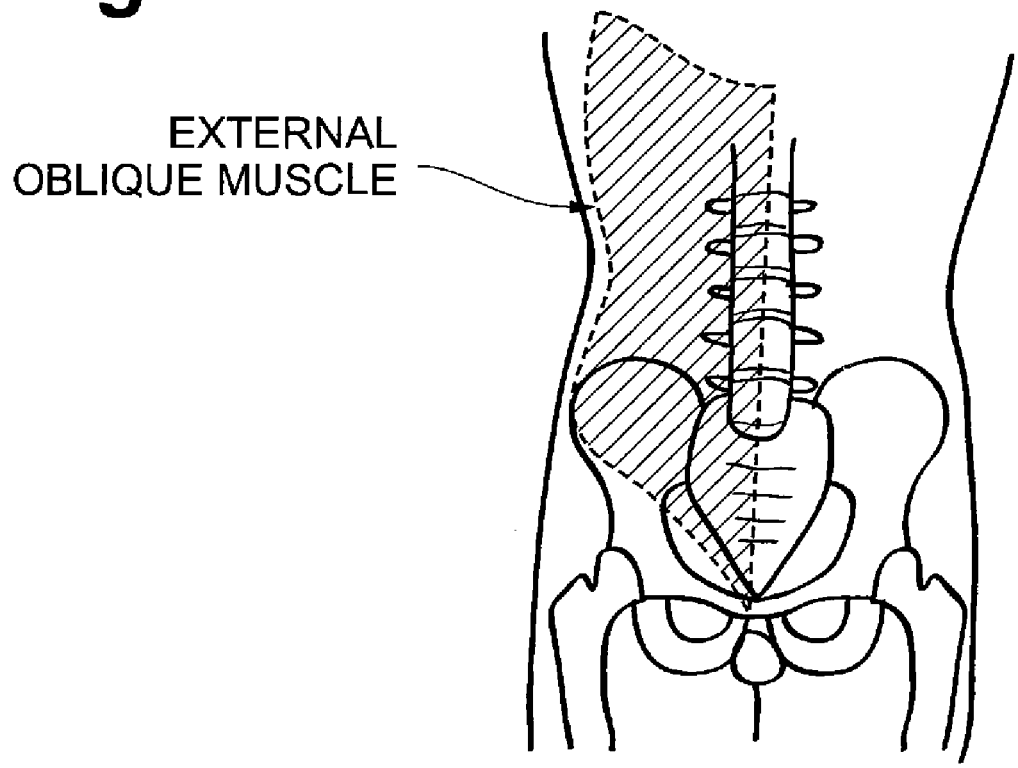
FIG. 1B is a figure for explaining the position of the external oblique muscle of the body.
Figure 2A:
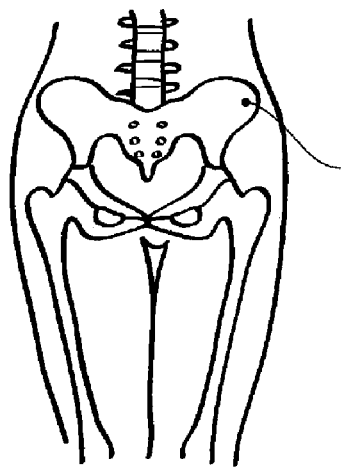
FIG. 2A is a figure for explaining the position of the ilium in a skeletal diagram for the case of viewing the body from the front.
Figure 2B:
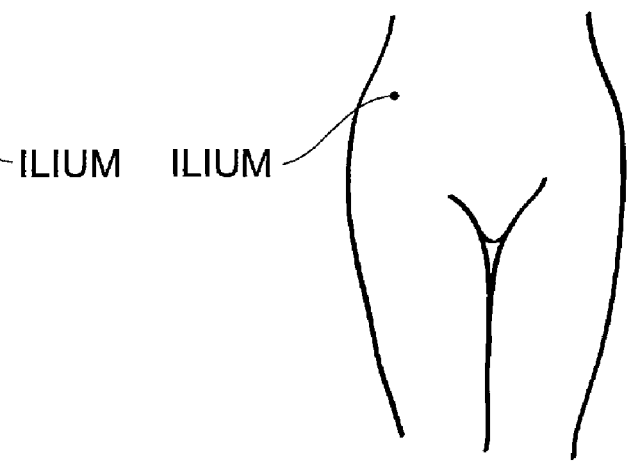
FIG. 2B is a figure for explaining the position of the ilium in an outline drawing for the case of viewing the body from the front.
Figure 2C:
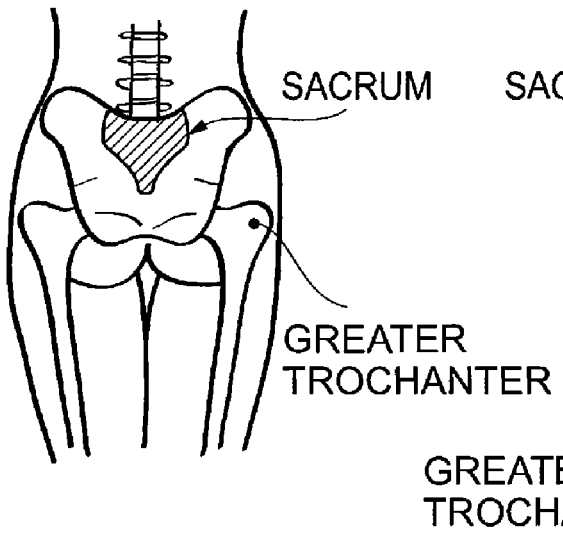
FIG. 2C is a figure for explaining the positions of the sacrum and the greater trochanters in a skeletal diagram for the case of viewing the body from the rear.
Figure 2D:
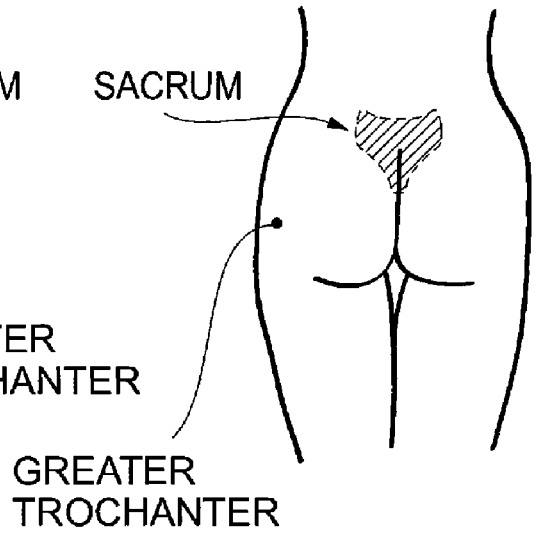
FIG. 2D is a figure for explaining the positions of the sacrum and the greater trochanters in an outline drawing for the case of viewing the body from the rear.

Embodiments of the present invention are described hereinafter with reference to the drawings. It should be noted that the same elements are given the same reference numerals; thus redundant repeated explanation will be omitted.

Figure 3A:
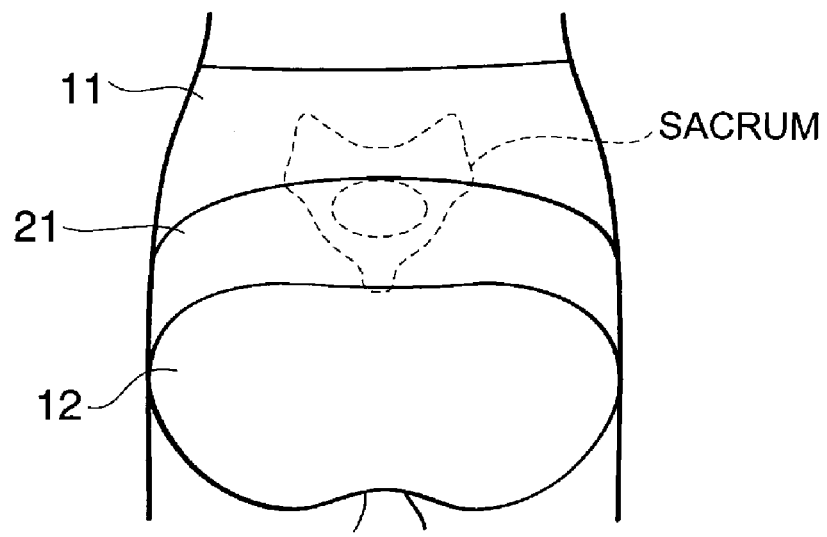
FIG. 3A is a back view of a state in which the garment is being worn, explaining the positional relation among a girdle of an embodiment, the ilium, sacrum, and greater trochanters of the body.
Figure 3B:
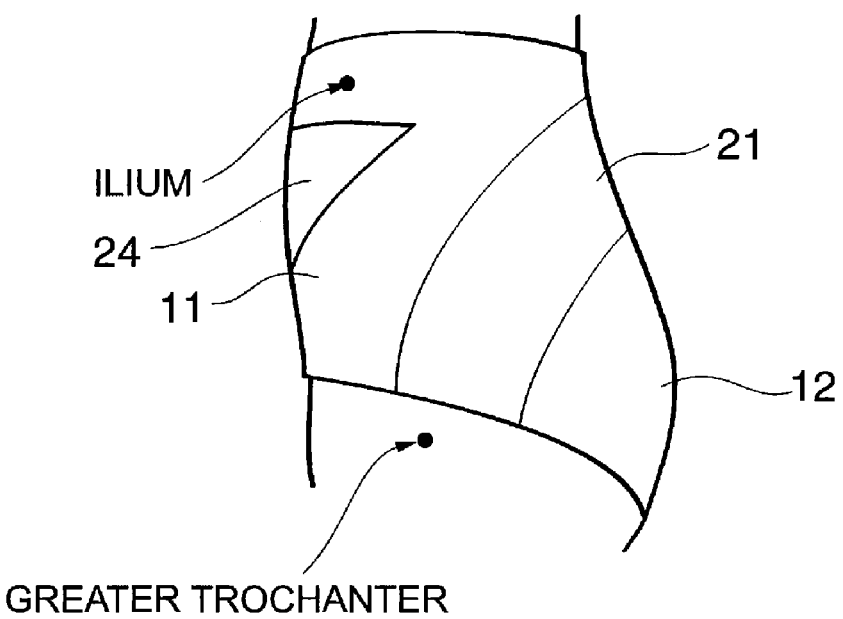
FIG. 3B is a side view of a state in which the garment is being worn, explaining the positional relation among the girdle of the embodiment, the ilium, sacrum, and greater trochanters of the body.

FIG. 3A and FIG. 3B show a crotch-possessing corrective garment (short-type girdle) according to an embodiment. FIG. 3A is a figure viewed from the rear of a state in which the girdle is being worn, and FIG. 3B is a figure viewed from the side. This girdle is configured by sewing together a front waist fabric portion 11 which fits over the front of the lower abdomen of the wearer, a hip fabric portion 12 which fits over the buttocks, a crotch fabric portion (not shown) which fits over the crotch, and a tightening fabric portion 21 which fits similarly over the body (lumbar region) of the wearer. The tightening fabric portion 21, which applies a tightening force to the lumbar region of the wearer, is provided in an area which suitably fits over the lumbar region so as to form a constituent of the garment (girdle) itself; thus handling is easy, and the feeling when worn is not impaired. Furthermore, the girdle has an inverted triangular body front tightening fabric portion 24 extending from an upper part of the front waist fabric portion 11 toward a somewhat lower part of same. This body front tightening fabric portion 24 is also made of material having a tightening force, and supports the external oblique muscles of the wearer.

When the garment is being worn, the tightening fabric portion 21 forms a belt shape having an approximately constant width which extends from above the buttocks cleft, passing above the right and left buttocks, to the vicinities of the right and left greater trochanters. Furthermore, the tightening fabric portion 21 is made of fabric for which the magnitude of the tightening force varies with areas, wherein the strongest tightening force acts in the vicinity of the upper part of the buttocks cleft, and the tightening portion which extends from the vicinities of the upper parts of the right and left buttocks cleft to the vicinities of the right and left greater trochanters weakens gradually. Moreover, the tightening fabric portion 21 is curved in a shape which is upwardly convex, and an uppermost part thereof fits above the buttocks cleft (in a lower position of the sacrum), as shown in FIG. 3A.

Figure 4:
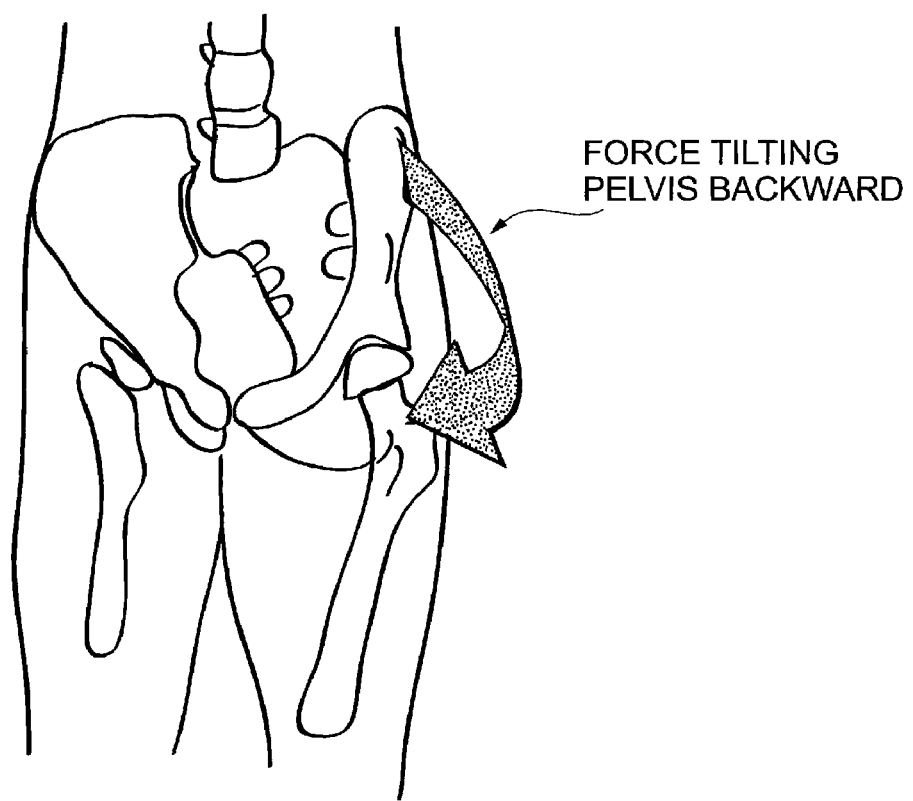
FIG. 4 is a figure for explaining the function of the embodiment from the skeleton in the lumbar region of the body.

According to the short girdle of the present embodiment, when the girdle is being worn, the tightening fabric portion 21, which extends from above the buttocks cleft, passing above the right and left buttocks, to the vicinities of the right and left greater trochanters, has an action of supporting the piriform muscles and pushing a somewhat lower part of the sacrum from the rear. Specifically, the strongest tightening force acts in the vicinity of the upper part of the buttocks cleft, and the tightening portion, which extends from the vicinities of the upper parts of the right and left buttocks to the vicinities of the right and left greater trochanters, becomes weak gradually; thus a force acts on the buttocks and the tension in the flank portions is reduced. Therefore, there is an action similar to allowing the buttocks to strain the muscles thereof to close the anus. The tightening force at the upper part of the buttocks cleft on the fabric of the girdle on the buttocks is strong, and a force which pushes the buttocks out and a force which makes the wearer's legs turn inward are generated. That is, as shown by the arrow in FIG. 4, a force which tilts the pelvis backward acts; thus the effect of improving the posture of the wearer whose pelvis tends to be tilted forward is achieved.

Figure 5:
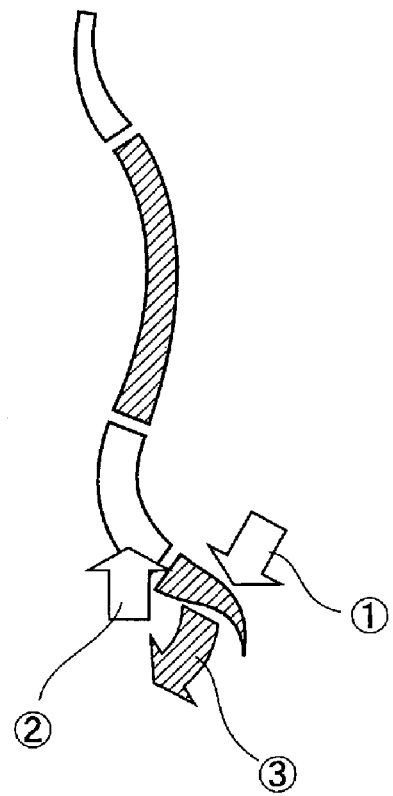
FIG. 5 is a figure for schematically explaining the function of the embodiment.

FIG. 5 schematically explains such an action. A force which supports the piriform muscles and pushes (a somewhat lower part of) the sacrum from the rear (arrow (1) in FIG. 5) acts, and a force which supports the external oblique muscles and reduces the forward curvature of the lumbar flexure (arrow (2) in FIG. 5) acts, and as a result a force which rotates the lumbar region backward from the front (arrow (3) in FIG. 5) is generated. Accordingly, the posture of the wearer whose pelvis tends to be tilted forward is improved.

It should be noted that there are three specific configurations of the tightening portion: first of all, a configuration in which the material of the tightening portion is "attached onto the fabric of the main body of the garment"; secondly a configuration in which the material of the tightening portion is "sewed together with the fabric of the main body of the garment"; and thirdly a configuration in which "the power is changed in a single piece of knitted fabric (circular knitting or warp knitting)." As an example, regarding warp knitting, the tightening portion can be made by using a single raschel jacquard, tricot jacquard or double raschel jacquard which is provided with an area having strong power by allowing the jacquard pattern to curve into a belt shape. Furthermore, the tightening portion can be made such that the tightening force is made strongest in the vicinity of a lower part of the sacrum and caused to become weak gradually in the direction in which the tightening portion extends.

Figure 6:
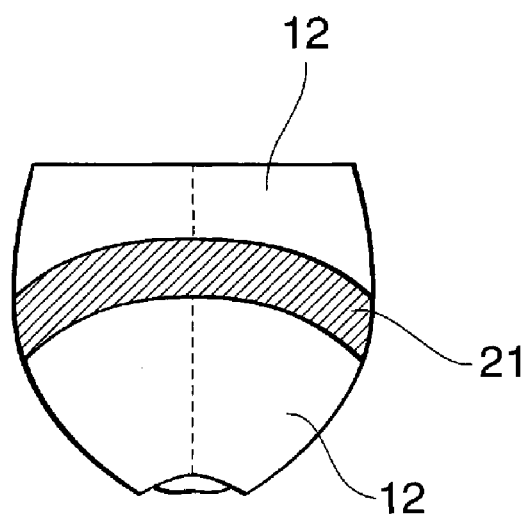
FIG. 6 is a figure showing a configuration of the rear of a short girdle according to the embodiment.
Figure 7A:
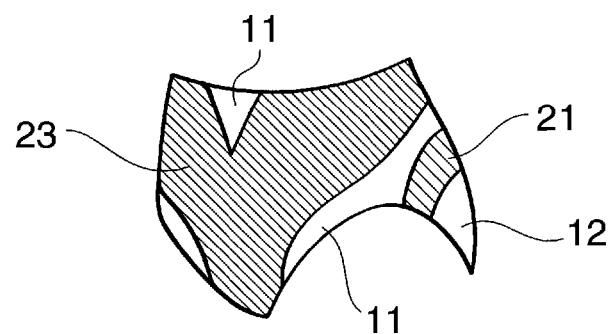
FIG. 7A is a figure showing an example of a front structure of the girdle according to the embodiment shown in FIG. 6.
Figure 7B:
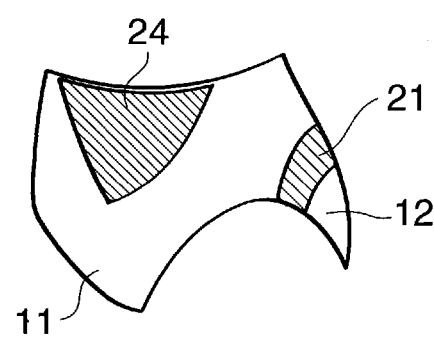
FIG. 7B is a figure showing an example of the front structure of the girdle according to the embodiment shown in FIG. 6.
Figure 7C:
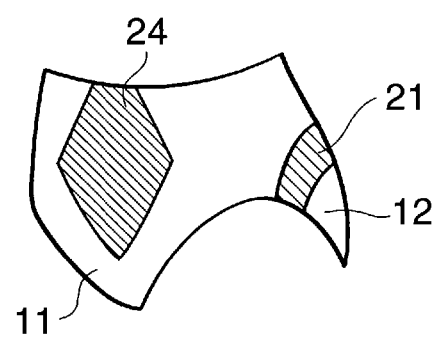
FIG. 7C is a figure showing an example of the front structure of the girdle according to the embodiment shown in FIG. 6.
Figure 7D:
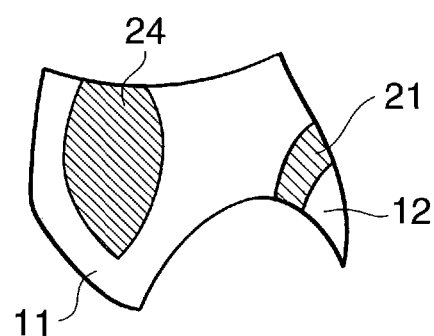
FIG. 7D is a figure showing an example of the front structure of the girdle according to the embodiment shown in FIG. 6.
Figure 7E:
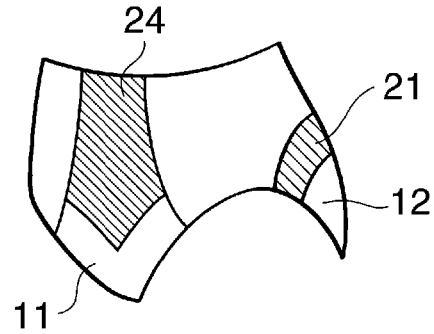
FIG. 7E is a figure showing an example of the front structure of the girdle according to the embodiment shown in FIG. 6.

FIG. 6 is a figure for the case of viewing the short-type girdle according to another embodiment from the rear when the garment is being worn. This girdle has a front waist fabric portion 11 (not shown), a hip fabric portion 12, and a crotch fabric portion (not shown), and is configured to have a tightening fabric portion 21 which is the same as the one in the embodiment of FIG. 3A and FIG. 3B.

FIG. 7A through FIG. 7E show front structures of the girdle according to the embodiment of FIG. 6. FIG. 7A through 7E are figures in which modified examples of the garment are viewed from the front left side, the modified examples being different from one another. The girdle shown in FIG. 7A has a body front tightening fabric portion 23 on the front waist fabric portion 11 to support the external oblique muscles. The body front tightening fabric portion 23 is made of material having a tightening force, and forms an approximately V-shape extending from the front center (above the crotch) upward to the right and left when the girdle is being worn. The girdle shown in FIG. 7B has an inverted triangular body front tightening fabric portion 24 on an upper part of the front waist fabric portion 11. This body front tightening fabric portion 24 is also made of material having a tightening force, and supports the external oblique muscles of the wearer. Moreover, the girdle shown in FIG. 7C has a diamond-shape body front tightening fabric portion 24 which extends from the upper part of the front waist fabric portion 11 toward the somewhat lower part of the same. The girdle shown in FIG. 7D has an oval body front tightening fabric portion 24 which extends from the upper part of the front waist fabric portion 11 toward the somewhat lower part of the same, and the girdle shown in FIG. 7E has a sword-shaped body front tightening fabric portion 24 which extends from the upper part of the front waist fabric portion 11 toward the somewhat lower part of the same. These body front tightening fabric portions 24 are made of material having a tightening force, and support the external oblique muscles of the wearer.

Figure 8:
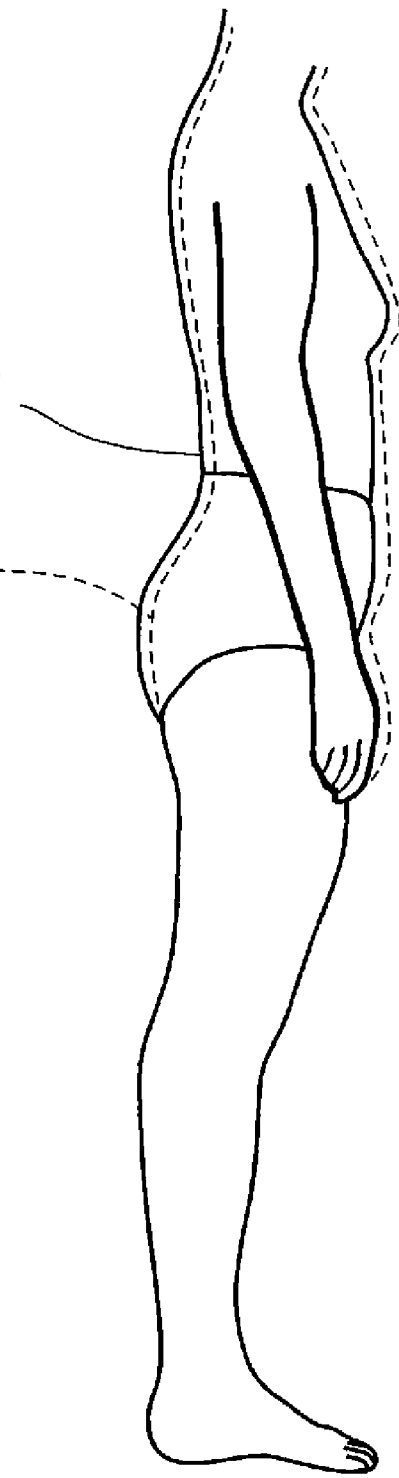
FIG. 8 is a figure for explaining the posture correction effect of a short girdle according to the embodiment.

FIG. 8 shows the posture-improving effect of a short girdle to which the present invention is applied. In FIG. 8 the dashed line shows the posture of a monitor in a nude state, and the solid line shows the posture of the monitor when wearing the girdle. It can be seen from FIG. 8 that the posture which tends to be tilted forward without the girdle is improved significantly. Furthermore, when wearing such a short girdle, there is the effect of not only correcting the posture, but also making movement of the lower half of the body smooth so that the stride is extended.

As in the embodiments of the present invention, supporting the piriform muscles along a line extending from the groin on the right and left thighs and passing the upper parts of the right and left hips to join at the upper part of the buttocks cleft (the line of the tightening fabric portion 21) is required for improving the posture, and then, by mainly supporting the external oblique muscles by means of lines which spread out from the front center of the front of the abdomen diagonally upward to the flanks (the lines of the body front tightening fabric portion 23, 24), the posture can be improved.

The present invention is not limited to the embodiments and modified examples described above; thus various other forms as shown in FIG. 9A through FIG. 14D can be applied.

Figure 9A:
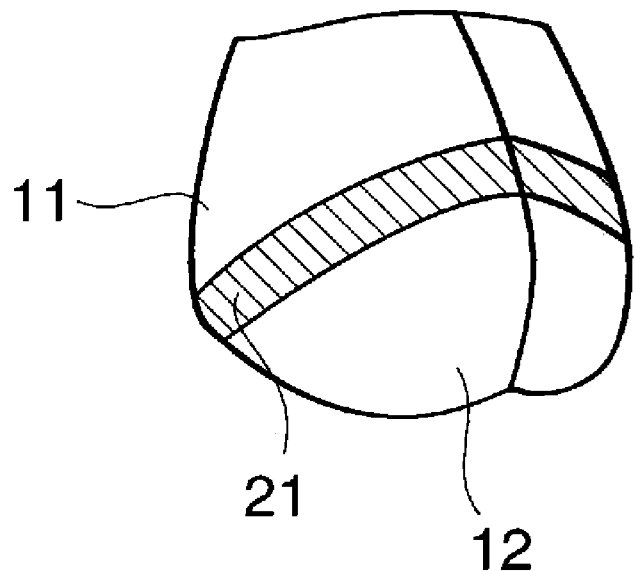
FIG. 9A is a rear perspective view of a short girdle showing a first modified example of the embodiment.
Figure 9B:
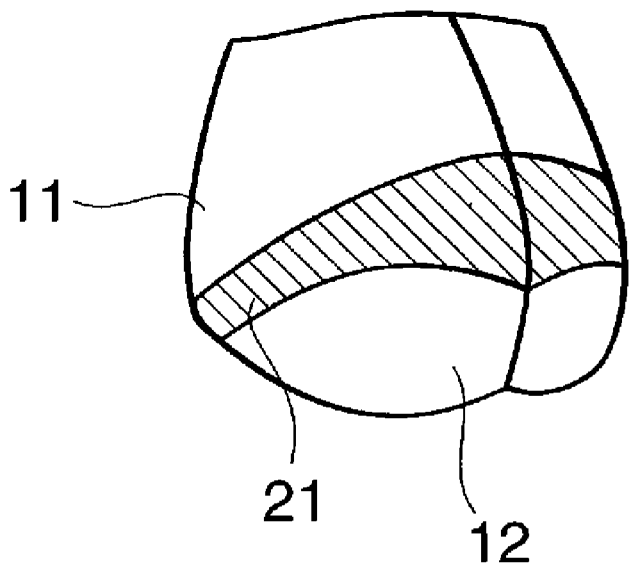
FIG. 9B is a rear perspective view of a short girdle showing a modified example of the embodiment.

FIG. 9A and FIG. 9B are perspective views in which short-type girdles according to a first modified example of the embodiment are viewed from the back. In each of the cases, the tightening fabric portion 21 extends from the vicinity of the upper part of the buttocks cleft, passing the vicinities of the upper parts of the right and left buttocks, to the vicinities of the right and left greater trochanters. Specifically, in the girdle shown in FIG. 9A, each of the pair of right and left tightening fabric portions 21 is configured so as to have a constant width up to above the buttocks cleft. In the girdle shown in FIG. 9B, each of the pair of right and left tightening fabric portions 21 is configured to have a wide width at the upper part of the buttocks cleft.

In each of the cases of FIG. 9A and FIG. 9B, the front waist fabric portion 11 is provided at the front of the tightening fabric portion 21, and the hip fabric portion 12 is provided at the rear of the same. Although the tightening fabric portion 21 of FIG. 9B covers the upper part of the buttocks cleft such that the fabric above the upper part of the buttocks cleft is wider, the region applied with a strong tightening force by the tightening fabric portion 21 is located in the vicinity of the upper part of the buttocks cleft, and a tightening fore acts in a direction passing the vicinities of the upper parts of the right and left buttocks toward the vicinities of the right and left greater trochanters; thus there is an action on the piriform muscles and the effect of improving the posture is excellent.

Figure 10A:
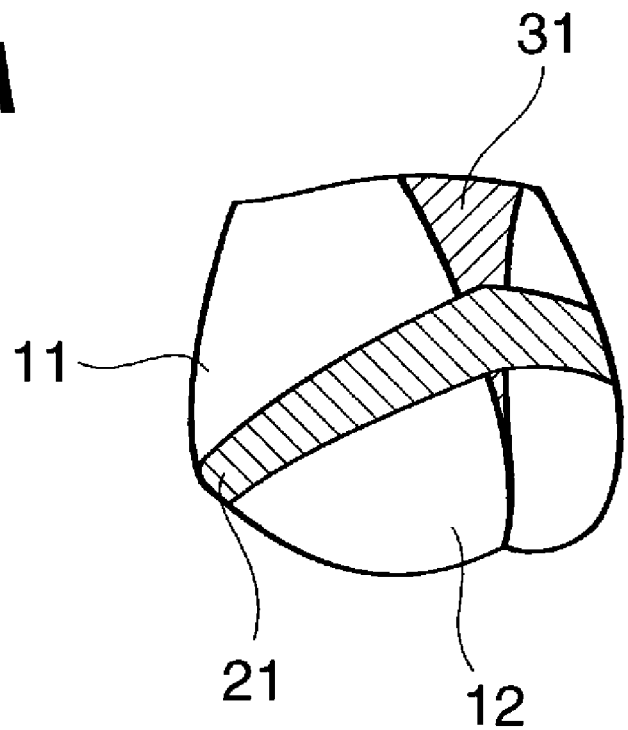
FIG. 10A is a rear perspective view of a short girdle showing a second modified example of the embodiment.
Figure 10B:
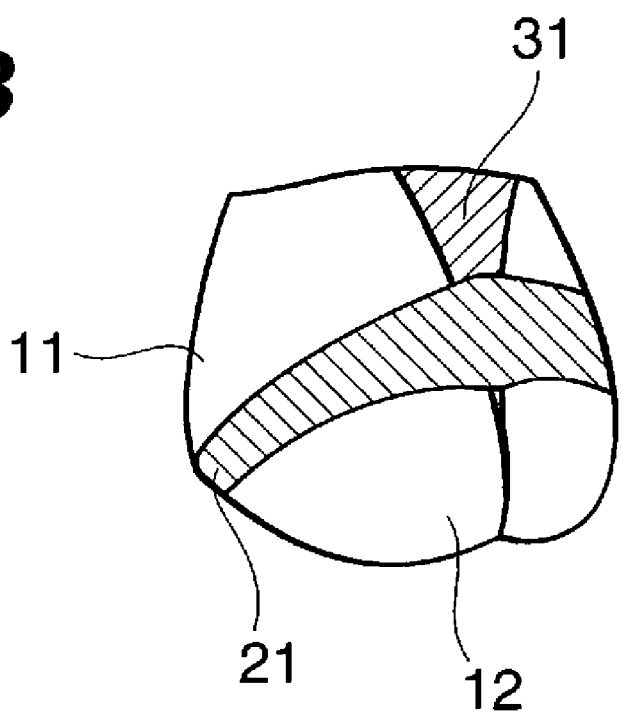
FIG. 10B is a rear perspective view of a short girdle showing another second modified example of the embodiment.

FIG. 10A and FIG. 10B are perspective views in which short-type girdles according to a second modified example of the embodiment are viewed from the rear. In this case as well, an inverted triangular rear center fabric portion 31 is sewed at the rear center of the lumbar region. Further, the tightening fabric portion 21 extends from the vicinity of the upper part of the buttocks cleft, passing the vicinities of the upper parts of the right and left buttocks, to the vicinities of the right and left greater trochanters. Specifically, in the girdle shown in FIG. 10A, each of the pair of right and left tightening fabric portions 21 is configured so as to have a constant width up to above the buttocks cleft. In the girdle shown in FIG. 10B, each of the pair of right and left tightening fabric portions 21 is configured to have a wide width at the upper part of the buttocks cleft.

In each of the cases of FIG. 10A and FIG. 10B, the front waist fabric portion 11 is provided at the front of the tightening fabric portion 21, and the hip fabric portion 12 is provided at the rear of the same. Although the tightening fabric portion 21 covers the upper part of the buttocks cleft such that the fabric above the upper part of the buttocks cleft is wider, the region applied with a strong tightening force by the tightening fabric portion 21 follows a somewhat lower side of the piriform muscles; thus, in the girdle of FIG. 10B in particular, there is an action on the piriform muscles and the effect of improving the posture is excellent.

Figure 11A:
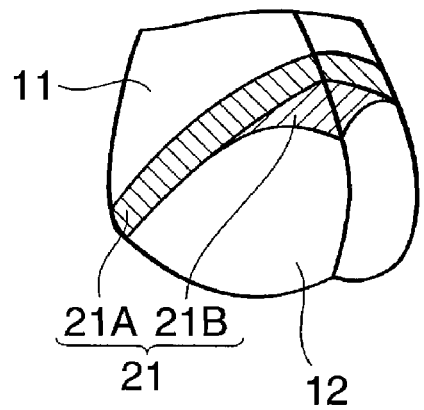
FIG. 11A is a rear perspective view of a short girdle showing a third modified example of the embodiment.
Figure 11B:
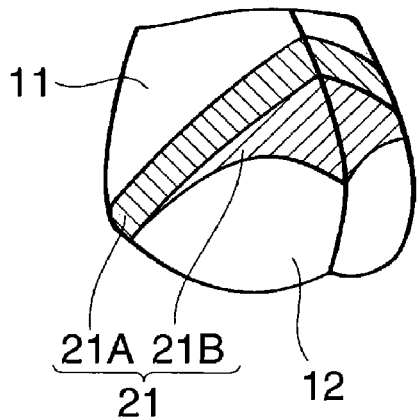
FIG. 11B is a rear perspective view of a short girdle showing another third modified example of the embodiment.
Figure 11C:
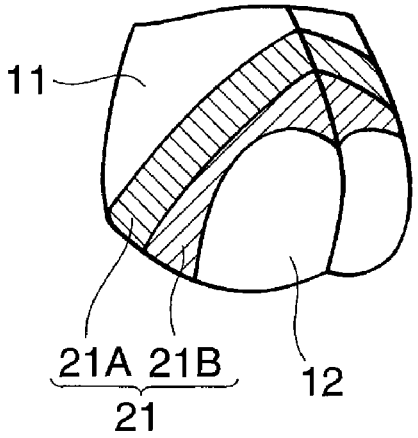
FIG. 11C is a rear perspective view of a short girdle showing another third modified example of the embodiment.

FIG. 11A through FIG. 11C are perspective views in which short-type girdles according to a third modified example of the embodiment are viewed from the rear. In each of the cases, the tightening fabric portion 21 covering the buttocks of the wearer is configured with an upper part 21A and a lower part 21B having a strong tightening force. Moreover, the front waist fabric portion 11 is provided at the front of the tightening fabric portion 21, and the hip fabric portion 12 is provided at the rear of the same.

The differences among FIG. 11A through FIG. 11C are the differences in the shape of the lower part 21B of each tightening fabric portion 21. In FIG. 11A the lower part 21B of the tightening fabric portion 21 covers a relatively narrow part in the vicinity of the upper part of the buttocks cleft. In FIG. 11B the lower part 21B of the tightening fabric portion 21 covers a relatively wide part extending from the upper part of the buttocks cleft to the buttocks cleft. In FIG. 11C the lower part 21B of the tightening fabric portion 21 covers a relatively wide part extending from the upper part of the buttocks cleft to the rear sides of the greater trochanters, so as to follow the upper part 21A.

In the case of the third modified example as well, the tightening force in the vicinity of the upper part of the buttocks cleft is strongest in the tightening fabric portion 21, and the tightening force acts in the direction passing the vicinities of the upper parts of the right and left buttocks to the vicinities of the right and left greater trochanters; thus there is an action on the piriform muscles and the effect of improving the posture is obtained. Particularly, the effect is large in the case of FIG. 11C. Moreover, since the tightening fabric portion 21 is configured with the upper part 21A and the lower part 21B, the tightening forces in these parts can be set differently.

Figure 12:
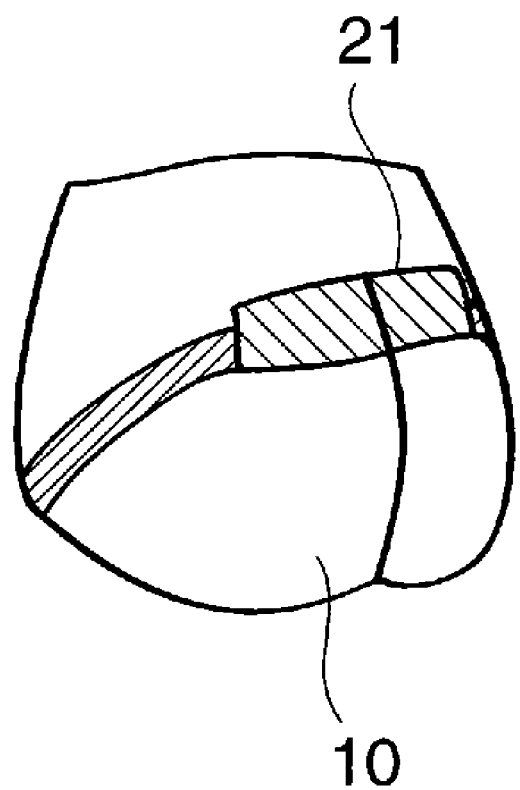
FIG. 12 is a rear perspective view of a short girdle showing a fourth modified example of the embodiment.

FIG. 12 is a perspective view in which a short-type girdle according to a fourth modified example of the embodiment is viewed from the back. The front waist fabric portion and the hip fabric portion are not configured separately but are integrated to constitute a girdle main body 10, wherein a rectangular tightening fabric portion 21 which extends to the right and left when the garment is being worn is provided above the buttocks cleft. In the case of the fourth modified example as well, the area with a large tightening force in the tightening fabric portion 21 is located in the vicinity of the upper part of the buttocks cleft.

Figure 13:
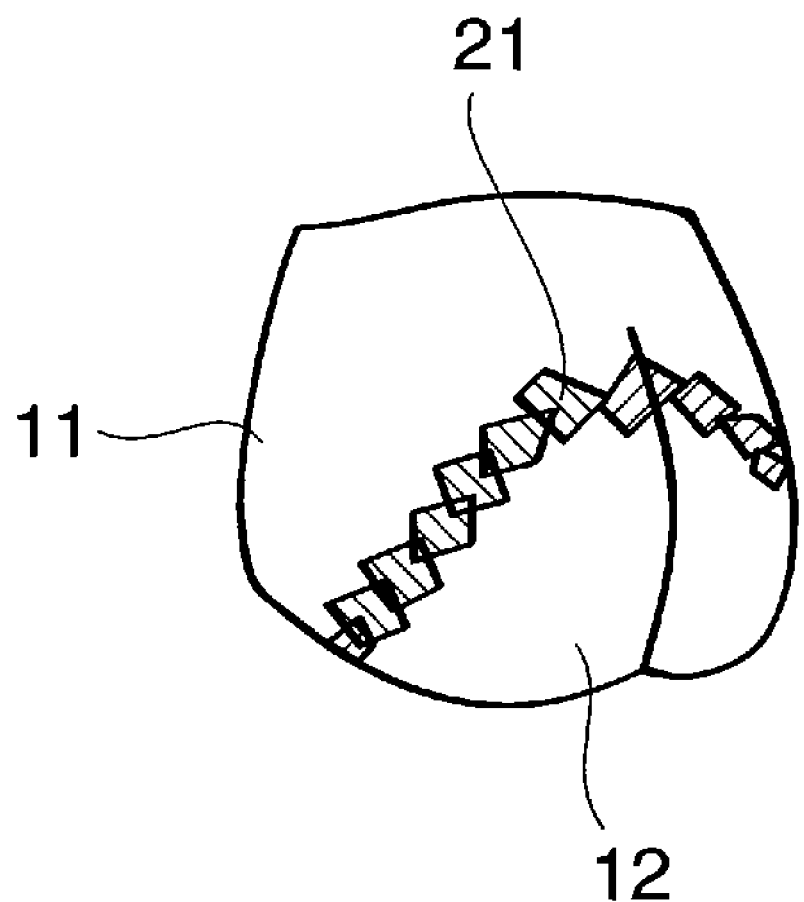
FIG. 13 is a rear perspective view of a short girdle showing a fifth modified example of the embodiment.

FIG. 13 is a perspective view in which a short-type girdle according to a fifth modified example of the embodiment is viewed from the back. The front waist fabric portion 11 is positioned at the front of the tightening fabric portion 21, the hip fabric portion 12 is positioned at the rear of the same, and the tightening fabric portion 21 extends from the upper part of the buttocks cleft to the vicinities of the greater trochanters. The tightening fabric portion 21 is configured by arranging a plurality of diamond-shape patches in line.

Figure 14A:
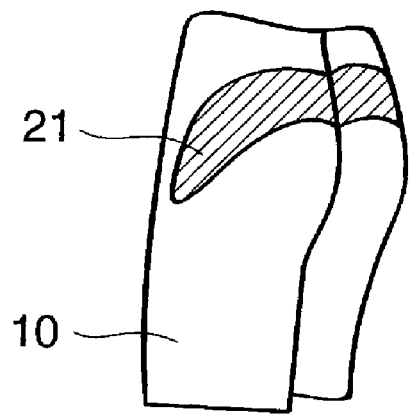
FIG. 14A is a rear perspective view of a long girdle showing a sixth modified example of the embodiment.
Figure 14B:
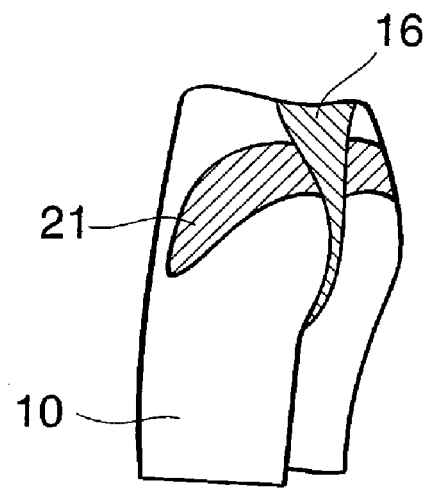
FIG. 14B is a rear perspective view of a long girdle showing another sixth modified example of the embodiment.
Figure 14C:
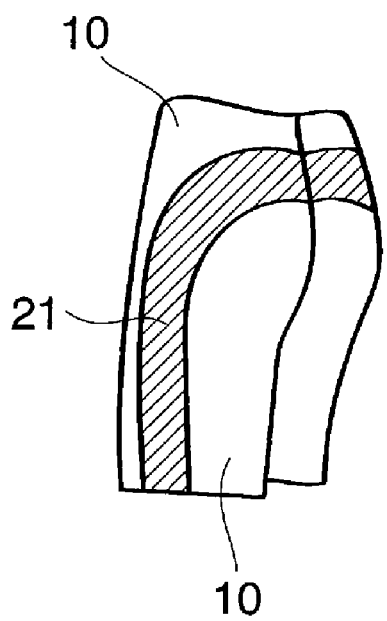
FIG. 14C is a rear perspective view of a long girdle showing another sixth modified example of the embodiment.
Figure 14D:
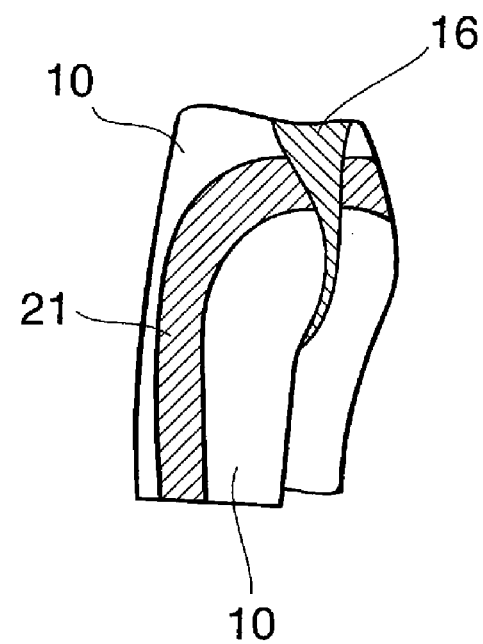
FIG. 14D is a rear perspective view of a long girdle showing another sixth modified example of the embodiment.
Figure 15A:
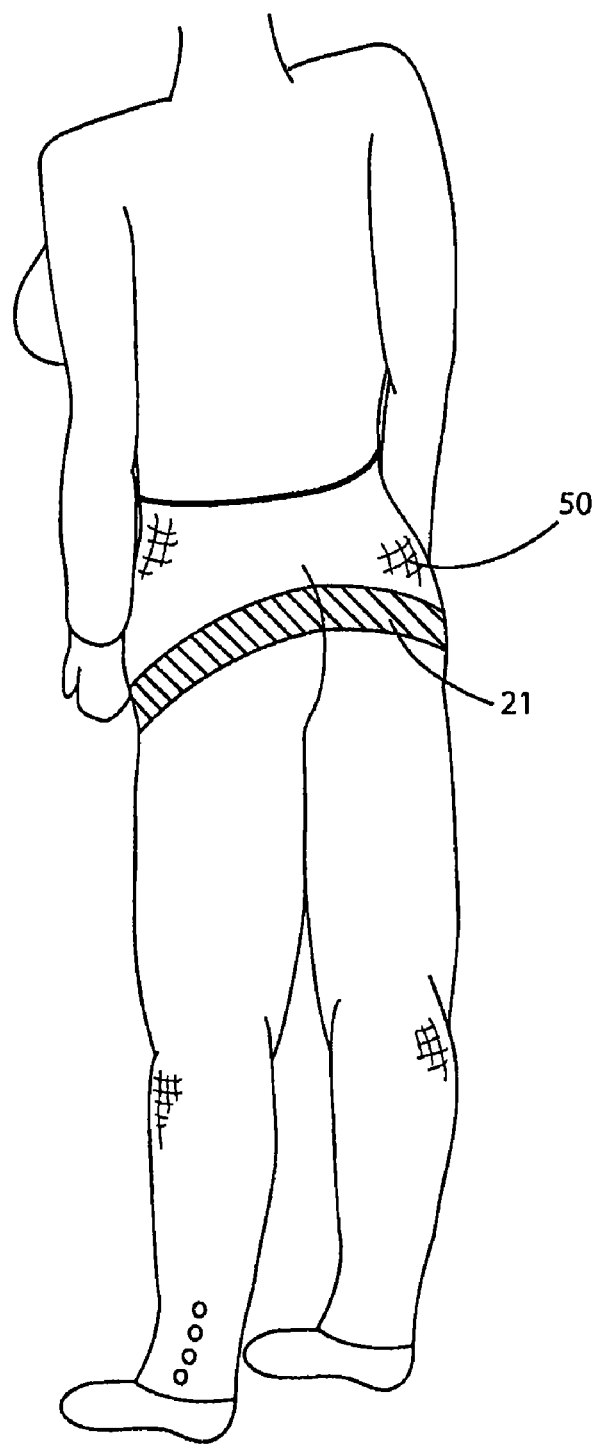
FIG. 15A is a rear perspective view of a spat according to another embodiment of the present invention.
Figure 15B:
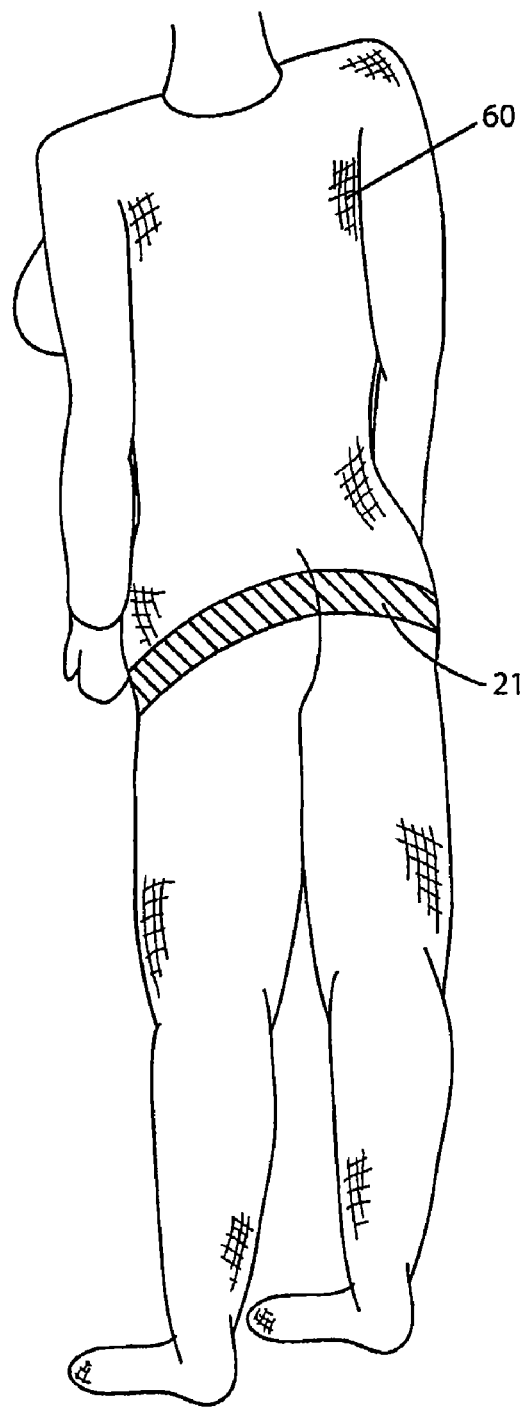
FIG. 15B is a rear perspective view of a leotard according to another embodiment of the present invention.
Figure 15C:
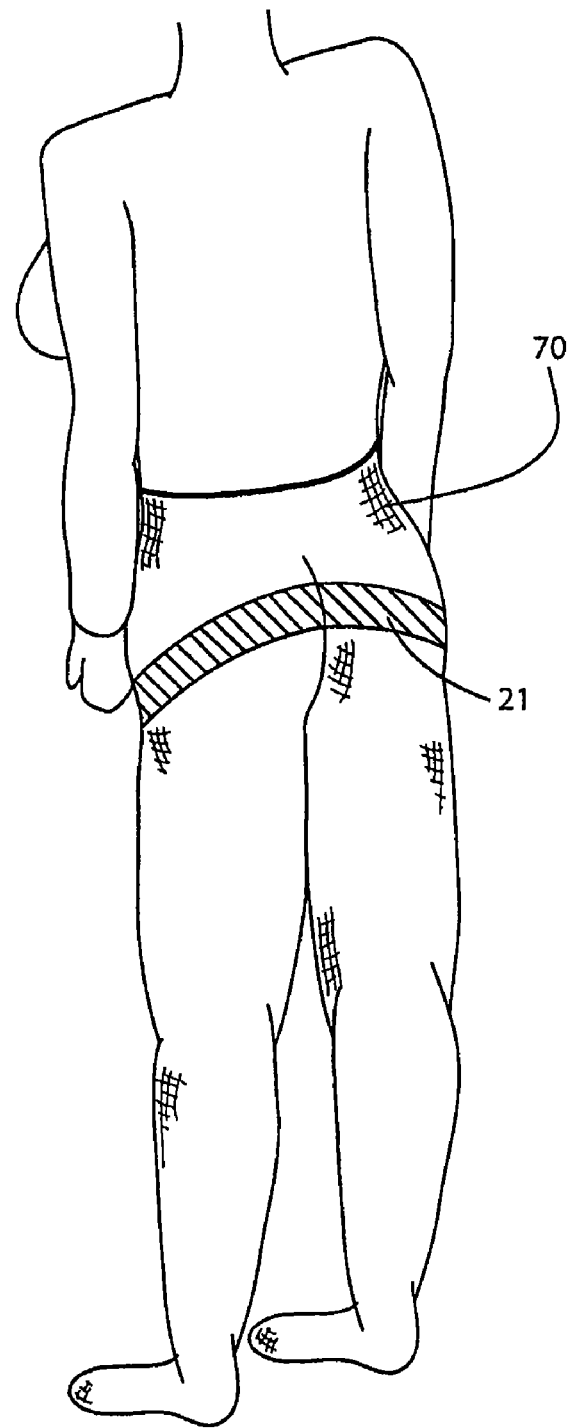
FIG. 15C is a rear perspective view of a tights according to another embodiment of the present invention.
Figure 15D:
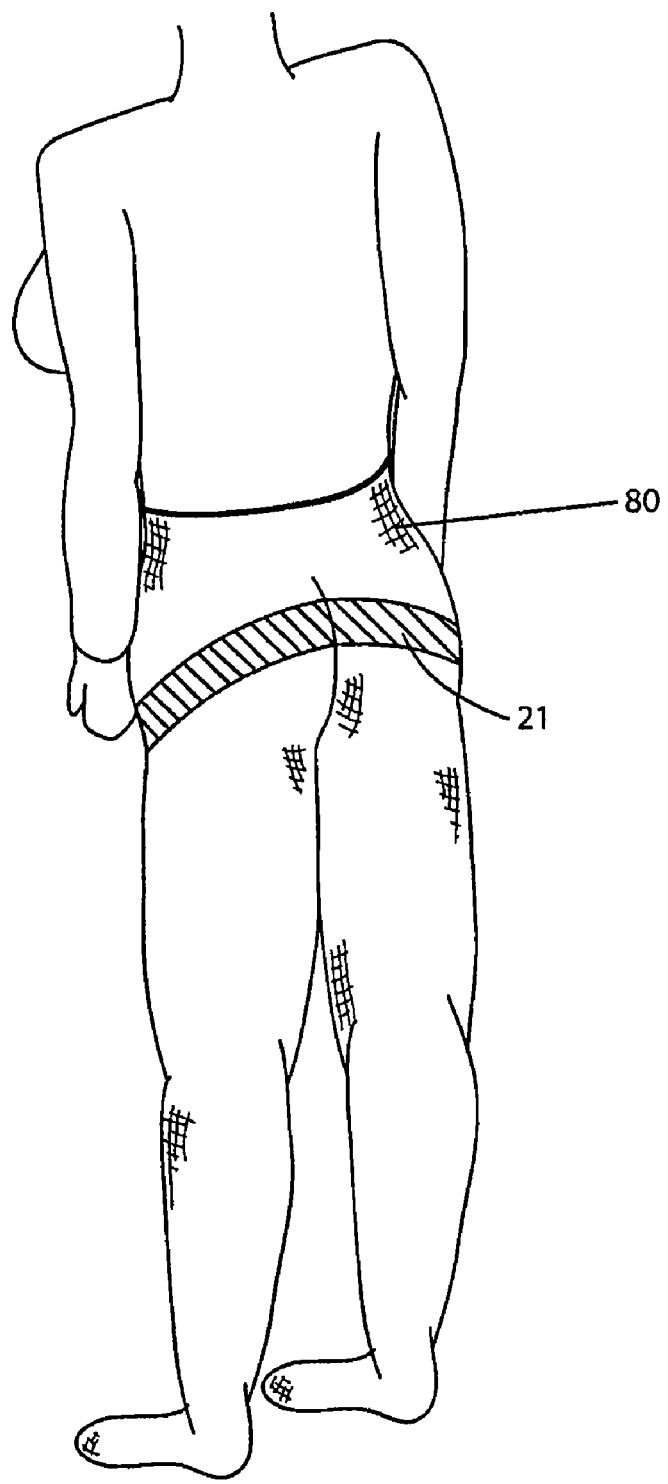
FIG. 15D is a rear perspective view of a pantyhose according to another embodiment of the present invention.
Figure 15E:
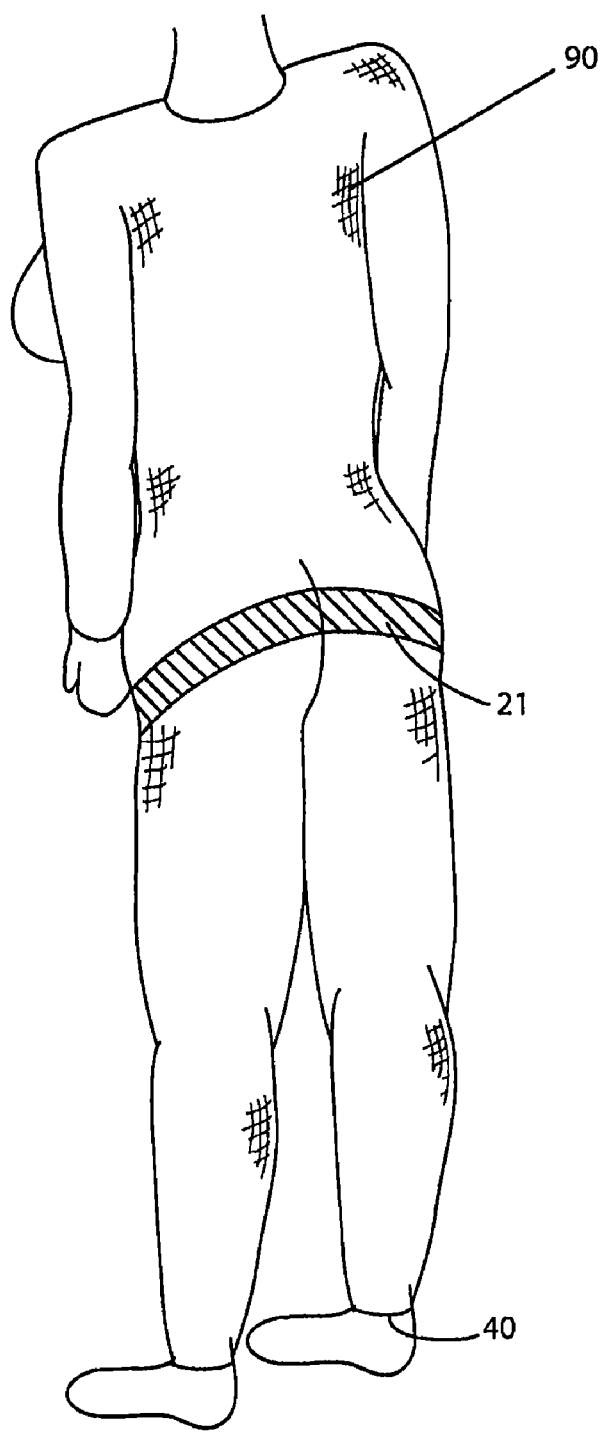
FIG. 15E is a rear perspective view of a sports tight according to another embodiment of the present invention.
Figure 15F:
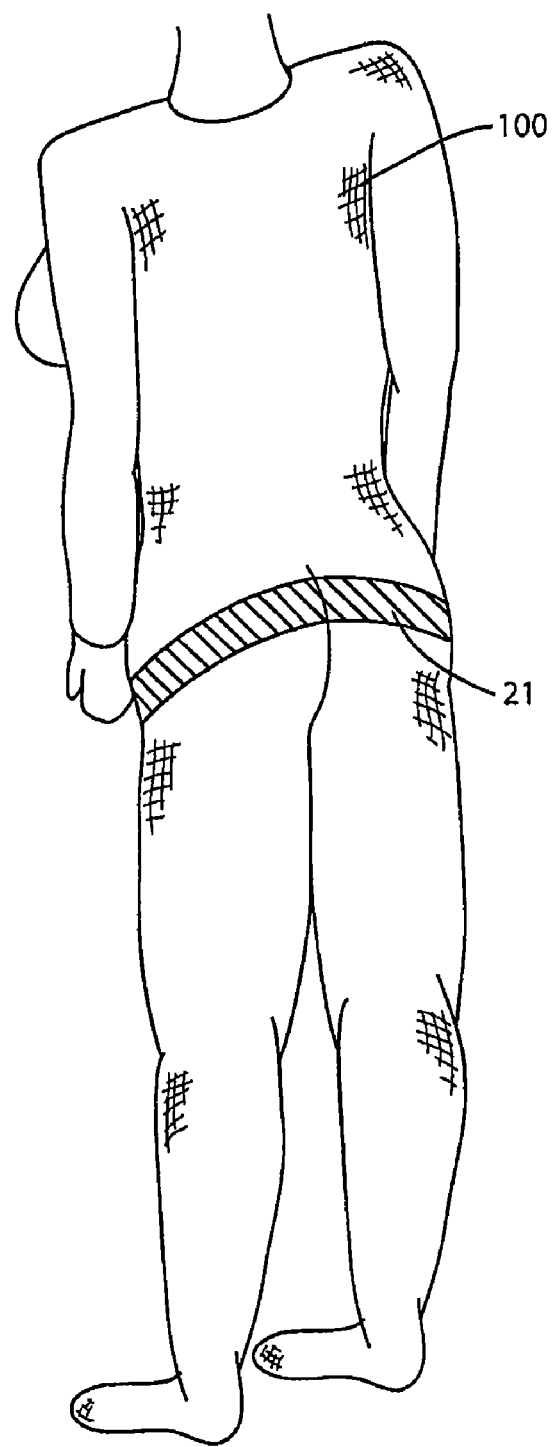
FIG. 15F is a rear perspective view of a bodysuit according to another embodiment of the present invention.
Figure 15G:
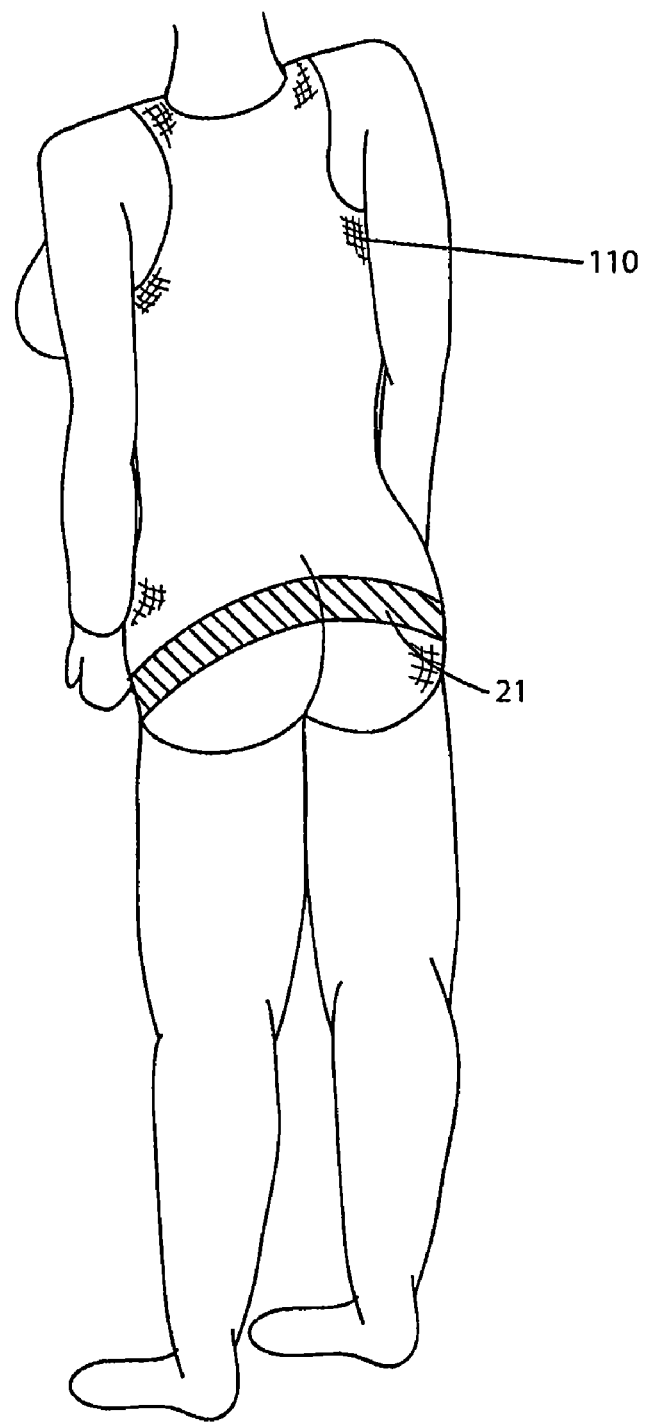
FIG. 15G is a rear perspective view of a bathing suit according to another embodiment of the present invention.

FIG. 14A through FIG. 14D are side views showing long-type girdles according to a sixth modified example of the embodiment. In each of the cases of FIG. 14A through FIG. 14D, the girdle fabric portion 10 extends from the lumbar region through the buttocks of the wearer to cover the femur part. The tightening fabric portion 21, which applies a tightening force from the lumbar region to the buttocks of the wearer, extends from the upper part of the buttocks cleft to the vicinities of the greater trochanters, and in the examples shown in FIG. 14C and FIG. 14D, it further extends downward from the vicinities of the greater trochanters to reach the vicinities of knee portions. It should be noted that the difference between FIG. 14A and FIG. 14B and the difference between FIG. 14C and FIG. 14D are that each of the girdles of FIG. 14B and FIG. 14D has an inverted triangular patch 16 in the vicinity of the buttocks cleft. The present invention is not limited to the embodiments described above, and various other modifications are possible. For example, the present invention may be applied to any one of a girdle, spats 50, a bathing suit 110, tights 70, a pantyhose 80, sports tights 90, a leotard 60, a body suit 100, men's pants and the like.

INDUSTRIAL APPLICABILITY

According to the crotch-possessing corrective garment of the present invention, the tightening portion applying a tightening force to the wearer's body fits over the wearer's body so as to form a constituent of the garment itself, and functions so as to support the piriform muscles and push a somewhat lower part of the sacrum from the rear. In this manner, the posture of the wearer whose posture tends to be tilted forward can be improved by acting on the muscles around the pelvis, such as the piriform muscles and the external oblique muscles, handling can be made easy, and the garment can be worn with no uncomfortable feeling.

What is claimed is:

1. A crotch-possessing corrective garment, comprising:
an integrated tightening portion in an area which fits over a wearer's body, the tightening portion extending, when the garment is being worn, from a vicinity of an upper part of a buttocks cleft, passing vicinities of upper parts of a right and left buttocks, to vicinities of a right and left greater trochanters; and
a body front tightening portion made of material having a tightening force and extending, when the garment is being worn, from above a crotch at a front center toward above a right and left of the crotch.

2. The crotch-possessing corrective garment according to claim 1, wherein the magnitude of a tightening force of the tightening portion varies along the area.

3. A crotch-possessing corrective garment, comprising:
an integrated right tightening portion and an integrated left tightening portion in areas fitting over a wearer's body, each of the tightening portions extending, when the garment is being worn, from the vicinity of the right or left greater trochanter to the vicinity of an upper part of the right or left buttocks and toward the vicinity of an upper part of the buttocks cleft; and
a body front tightening portion made of material having a tightening force and extending, when the garment is being worn, from above the crotch at the front center toward above the right and left of the crotch.

4. The crotch-possessing corrective garment according to claim 2, wherein the tightening force of the tightening portion is strongest in the vicinity of the upper part of the buttocks cleft.

5. The crotch-possessing corrective garment according to claim 4, wherein the tightening force of the tightening portion gradually weakens in a direction passing the vicinities of the upper parts of the right and left buttocks and extending toward the vicinities of the right and left greater trochanters.

6. The crotch-possessing corrective garment according to claim 1, further comprising thigh portions which fit over the wearer's thighs, wherein the tightening portion further extends from the vicinities of the greater trochanters along the outer borders of the thigh portions.

7. The crotch-possessing corrective garment according to claim 6, wherein the tightening portion further reaches ankles.

8. The crotch-possessing corrective garment according to claim 1, wherein the tightening portion has a shape which is curved upward in the vicinity of the upper parts of the buttocks when the garment is being worn.

9. The crotch-possessing corrective garment according to claim 1, wherein, when the garment is being worn, the tightening portion comprises:
an upper side tightening portion positioned on an upper side; and
a lower side tightening portion which is positioned on a lower side and has a strong tightening force.

10. The crotch-possessing corrective garment according to claim 1, wherein the tightening portion forms a belt shape.

11. The crotch-possessing corrective garment according to claim 1, wherein the tightening portion is formed through power change in a single piece of knitted fabric.

12. The crotch-possessing corrective garment according to claim 1, wherein the crotch-possessing corrective garment is any one of a girdle, spats, a bathing suit, tights, a pantyhose, sports tights, a leotard, a body suit, and men's pants.

13. The crotch-possessing corrective garment according to claim 3, wherein magnitudes of tightening forces of the tightening portions vary along the areas.

14. The crotch-possessing corrective garment according to claim 13, wherein the tightening forces of the tightening portions are strongest in the vicinity of the upper part of the buttocks cleft.

15. The crotch-possessing corrective garment according to claim 14, wherein the tightening forces of the tightening portions gradually weaken in directions passing the vicinities of the upper parts of the right and left buttocks and extending toward the vicinities of the right and left greater trochanters.

16. The crotch-possessing corrective garment according to claim 3, further comprising thigh portions which fit over the wearer's thighs, wherein the tightening portions further extend from the vicinities of the greater trochanters along the outer borders of the thigh portions.

17. The crotch-possessing corrective garment according to claim 16, wherein the tightening portions further reach ankles.

18. The crotch-possessing corrective garment according to claim 3, wherein, when the garment is being worn, each of the tightening portions comprises:
an upper side tightening portion positioned on an upper side; and
a lower side tightening portion which is positioned on a lower side and has a strong tightening force.

19. The crotch-possessing corrective garment according to claim 3, wherein the tightening portions are formed through power change in a single piece of knitted fabric.

20. The crotch-possessing corrective garment according to claim 3, wherein the crotch-possessing corrective garment is any one of a girdle, spats, a bathing suit, tights, a pantyhose, sports tights, a leotard, a body suit, and men's pants.

* * * * *